United States Patent [19]

Igarashi et al.

[11] Patent Number: 5,300,520
[45] Date of Patent: Apr. 5, 1994

[54] WOOD PRESERVATIVE COMPOSITION

[75] Inventors: Akira Igarashi; Koh Ogura; Masayuki Asai; Kazuya Okubo, all of Hyogo; Yosei Kuwazuru, Osaka, all of Japan

[73] Assignee: Takeda Chemical Industries, Ltd., Osaka, Japan

[21] Appl. No.: 690,668

[22] Filed: Apr. 24, 1991

[30] Foreign Application Priority Data

Apr. 25, 1990 [JP] Japan .................... 1-09015

[51] Int. Cl.$^5$ .................... A01N 37/00; A01N 43/64; A01N 43/78; A01N 47/10
[52] U.S. Cl. .................... 514/367; 514/383; 514/478; 514/479; 514/506; 514/512; 514/600; 514/720
[58] Field of Search ............ 514/478, 479, 367, 383, 514/506, 512, 600, 720

[56] References Cited

U.S. PATENT DOCUMENTS 4,871,766 10/1989 Tsuda et al. .................... 514/479
4,977,186 12/1990 Gruening .................... 514/479

FOREIGN PATENT DOCUMENTS 2185685 7/1987 United Kingdom .

OTHER PUBLICATIONS

Japanese Patents Gazette, week Y09, Apr. 11, 1977, Section Ch: Chemical, p. 6, Accession No. 15539Y/09, Derwent Publications Ltd., London, Great Britain.

*Primary Examiner*—Allen J. Robinson
*Attorney, Agent, or Firm*—Wenderoth, Lind & Ponack

[57] ABSTRACT

A wood preservative composition which comprises a wood preservative in an amount of 0.01–10% by weight and a diphenylalkane compound represented by the general formula

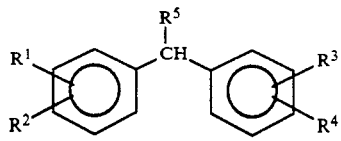

wherein $R^1$, $R^2$, $R^3$, $R^4$ and $R^5$ are independently hydrogen or an alkyl, in an amount of not less than 1% by weight and in an amount of 1–1000 parts by weight in relation to one part by weight of the wood preservative.

3 Claims, No Drawings

WOOD PRESERVATIVE COMPOSITION

This invention relates to a wood preservative composition.

There are already known a variety of wood preservatives which are germicidal or fungicidal, and hence provide wood with resistance to decay, however, such any known wood preservative is remains unsatisfactory in effectiveness and durability.

Meanwhile, it is known that a diphenylalkane compound of a specific type such as phenylxylylethane is useful as a solvent in an organic phosphorous emulsion insecticide to make it odorless, as described in Japanese Patent Publication No. 56-19841, Japanese Patent Application Laid-open No. 53-91139 and No. 58-57301. There is disclosed in Japanese Patent Application Laid-open No. 62-29501, a solid insectide which contains phenylxylylethane and has improved storage stability.

It is an object of the invention to provide a wood preservative composition which is improved in effectiveness and durability.

In accordance with the invention, there is provided a wood preservative composition which comprises a wood preservative in an amount of 0.01–10% by weight and a diphenylalkane compound represented by the general formula

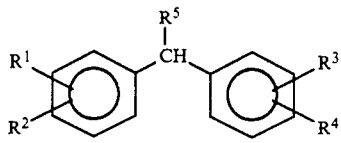

wherein $R^1$, $R^2$, $R^3$, $R^4$ and $R^5$ are independently hydrogen or an alkyl, in an amount of not less than 1% by weight and in an amount of 1–1000 parts by weight in relation to one part by weight of the wood preservative.

The wood preservative used is such that it is germicidal or fungicidal especially to rotting fungi such as *Tyromyces palustris, Coriolus versicolor, Serpula lacrymans* and *Pycnoporus coccineus*.

There may be mentioned as such a wood preservative, for example, an organoiodic compound such as 3-iodo-2-propynylbutylcarbamate (A-1), 3-bromo-2,3-diiodo-2-propenylethyl carbonate (A-2), p-chlorophenyl-3-iodopropargylformal (A-3), p-chlorophenyldiiodomethyl sulfone, 4-methylphenyldiiodomethyl sulfone or 2,3,3-triiodoallyl alcohol (TIAA); a benzimidazole or a benzthiazole compound such as 2-(4-thiazolyl)benzimidazole (TBZ), 1H-benzimidazol-2-yl-carbamic acid methyl ester or 2-thiocyanomethylthiobenzoimidazole (A-4); a triazole compound such as 1-((2-(2',4'-dichlorophenyl)-4-propyl-1,3-dioxolan-2-yl)methyl)-1H-1,2,4-triazole (A-5) or α-(2-(4-chlorophenyl)ethyl-α-(1,1-dimethylethyl)-1H-1,2,4-triazole-1-ethanol; a haloalkylthio wood preservative such as N,N-dimethyl-N'-phenyl-(N'-fluorodichloromethylthio)sulfamide (A-6) or N-fluorodichloromethylthiophthalimide. Tetrachloro-4-methylsulfonylpyridine or tetrachloroisophthalonitrile may also be used as a wood preservative. These wood preservatives may be used singly or as a mixture.

The wood preservative is contained in the composition of the invention in an amount of 0.01–10% by weight, preferably 0.05–2% by weight, and most preferably 0.1–1% by weight based on the composition.

The wood preservative composition of the invention contains the before mentioned diphenylalkane compound represented by the general formula. In the formula, the alkyl is preferably an alkyl of 1–3 carbons, and in particular the alkyl on the aromatic nuclei is preferably methyl. Further, the diphenylalkane compound is preferably such that at least one of the aromatic nuclei is a xylyl group. Accordingly, there may be exemplified as such a diphenylalkane compound, for example, phenylxylylethane, phenylxylylpropane, trixylylethane, dixylylmethane and dixylylethane. Among these is most preferred phenylxylylethane. However, the diphenylalkane compound may be used singly or as a mixture.

The diphenylalkane compound is contained in the composition in an amount of not less than 1% by weight, preferably not less than 5% by weight, and most preferably not less than 10% by weight. Further, it is necessary that the diphenylalkane compound is contained in the composition in an amount of 1–1000 parts by weight, preferably 5–500 parts by weight, and most preferably 10–200 parts by weight, in relation to one part by weight of the wood preservative.

The wood preservative composition may be composed of a wood preservative and the diphenylalkane compound, but it may contain other active ingredients. The active ingredient may include, for example, antitermite agents such as organic phosphorous insecticides, e.g., phoxim, chlorpyrifos, fenitrothion, pyridaphenthion, isofenphos or prothiophos; carbamate insecticides, e.g., bassa or propoxur; or pyrethroid insecticides, e.g., permethrin, cyfluthrin, tralomethrin, fenvalerate, ethofenprox or Hoe-498; insect repellents; or synergists such as 1,1,1,2,7,8,8,8-octachloro-4-oxaheptane.

The wood preservative composition may further contain such an additive as antioxidants, UV absorbents, emulsifiers, colorants or thickeners, as well as resins such as alkyd resins, acrylic resins or chlorinated paraffins. A solvent such as an aromatic petroleum solvent or an aliphatic petroleum solvent may also be contained in the wood preservative composition.

The wood preservative composition of the invention may be used as is. The composition may be applied to wood by any conventional method. Namely, the composition may be coated on wood, or wood is dipped in the composition so that usually an amount of 100–300 g of the wood preservative is applied per square meter of wood.

The wood preservative composition of the invention is effective not only to rotting fungi such as Tyromyces palustris, Coriolus versicolor, Serpula lacrymans or Pycnoporus coccineus, but also to fungi such as Chaetomium or Tricoderma.

The invention will now be described in more detail with reference to examples, however, the invention is not limited thereto.

The following wood preservative compositions were prepared wherein parts designate by weight. In some of the compositions, an aliphatic petroleum solvent or an aromatic petroleum solvent was used; the former being mainly composed of paraffins and having an aniline point of 69, and the latter being mainly composed of alkylbenzenes and having an aniline point of 16. The mixed solvent used was composed of the aliphatic and the aromatic petroleum solvent in a weight ratio of 2/8. The alkyd resin used had 66% oil length by tall oil.

---

Example 1

-continued

| | |
|---|---|
| A-1: | 0.5 parts |
| Phenylxylylethane: | 94.5 parts |
| Alkyd resin: | 5.0 parts |

Example 2

| | |
|---|---|
| A-2: | 0.5 parts |
| Phenylxylylethane: | 94.5 parts |
| Alkyd resin: | 5.0 parts |

Example 3

| | |
|---|---|
| A-3: | 0.5 parts |
| Phenylxylylethane: | 94.5 parts |
| Alkyd resin: | 5.0 parts |

Example 4

| | |
|---|---|
| A-4: | 0.5 parts |
| Phenylxylylethane: | 94.5 parts |
| Alkyd resin: | 5.0 parts |

Example 5

| | |
|---|---|
| A-5: | 0.5 parts |
| Phenylxylylethane: | 94.5 parts |
| Alkyd resin: | 5.0 parts |

Example 6

| | |
|---|---|
| A-6: | 0.7 parts |
| Phenylxylylethane: | 94.3 parts |
| Alkyd resin: | 5.0 parts |

Example 7

| | |
|---|---|
| A-6: | 0.5 parts |
| Phenylxylylethane: | 94.5 parts |
| Alkyd resin: | 5.0 parts |

Example 8

| | |
|---|---|
| A-5: | 0.5 parts |
| Phenylxylylethane: | 99.5 parts |

Example 9

| | |
|---|---|
| A-5: | 0.5 parts |
| Phenylxylylethane: | 50.0 parts |
| Aliphatic petroleum solvent: | 49.5 parts |

Example 10

| | |
|---|---|
| A-5: | 0.5 parts |
| Phenylxylylethane: | 20.0 parts |
| Aliphatic petroleum solvent: | 79.5 parts |

Comparative Example 1

| | |
|---|---|
| A-1: | 1.0 parts |
| Mixed solvent: | 94.0 parts |
| Alkyd resin: | 5.0 parts |

Comparative Example 2

| | |
|---|---|
| A-2: | 0.5 parts |
| Aliphatic petroleum solvent: | 94.5 parts |
| Alkyd resin: | 5.0 parts |

Comparative Example 3

| | |
|---|---|
| A-3: | 0.5 parts |
| Mixed solvent: | 94.5 parts |
| Alkyd resin: | 5.0 parts |

Comparative Example 4

| | |
|---|---|
| A-4: | 1.0 parts |
| Aromatic petroleum solvent: | 94.0 parts |
| Alkyd resin: | 5.0 parts |

Comparative Example 5

| | |
|---|---|
| A-5: | 0.5 parts |
| Aliphatic petroleum solvent: | 94.5 parts |
| Alkyd resin: | 5.0 parts |

Comparative Example 6

| | |
|---|---|
| A-6: | 1.0 parts |
| Mixed solvent: | 94.0 parts |
| Alkyd resin: | 5.0 parts |

Comparative Example 7

| | |
|---|---|
| A-1: | 0.5 parts |
| Mixed solvent: | 94.5 parts |
| Alkyd resin: | 5.0 parts |

Comparative Example 8

| | |
|---|---|
| A-2: | 1.0 parts |
| Aliphatic petroleum solvent: | 94.0 parts |
| Alkyd resin: | 5.0 parts |

Comparative Example 9

| | |
|---|---|
| A-6: | 0.5 parts |
| Mixed solvent: | 94.5 parts |
| Alkyd resin: | 5.0 parts |

Comparative Example 10

| | |
|---|---|
| A-5: | 0.5 parts |
| Aliphatic petroleum solvent: | 99.5 parts |

TEST EXPERIMENT 1

The wood preservative compositions prepared in the Examples 1-6 and Comparative Examples 1-6 were each applied to a test piece of sapwood of beech of 40 mm length, 20 mm wide and 5 mm thick at a rate of 100–120 g/m$^2$ by a dipping method and air-dried, followed by measurement of average decrease in weight of the test piece in accordance with the preservative effect of standardized test method No. 1 of the Japan Wood Preservation Association. As contrast tests, a test piece to which the preservative was not applied was also tested in the same manner.

Coriolus versicolor was used as fungus. Weathering resistance test was carried out as follows. After the application of the composition and air-drying, the test pieces were immersed in distilled water at 25° C. for 5 hours, and then placed in a hot air oven at 40° C. for 19 hours. These operations were repeated 30 times. The results are shown in the Table 1.

TABLE 1

| | Wood Preservative Composition | | |
|---|---|---|---|
| | Wood Preservative and Its Content in the Composition (weight %) | | Content of Phenylxylyl-ethane (weight %) | Average Decrease in Weight (weight %) |
| Example 1 | A-1 | 0.5 | 94.5 | 1.3 |
| Comparative 1 | A-1 | 1.0 | — | 3.9 |
| Example 2 | A-2 | 0.5 | 94.5 | 2.2 |
| Comparative 2 | A-2 | 0.5 | — | 13.1 |
| Example 3 | A-3 | 0.5 | 94.5 | 1.6 |
| Comparative 3 | A-3 | 0.5 | — | 9.4 |
| Example 4 | A-4 | 0.5 | 94.5 | 2.6 |
| Comparative 4 | A-4 | 1.0 | — | 14.2 |
| Example 5 | A-5 | 0.5 | 94.5 | 1.0 |
| Comparative 5 | A-5 | 0.5 | — | 6.7 |
| Example 6 | A-6 | 0.7 | 94.3 | 1.4 |
| Comparative 6 | A-6 | 1.0 | — | 13.1 |
| Contrast | — | — | — | 32.8 |

TEST EXPERIMENT 2

Wood preservative test was carried out with the wood preservative compositions shown in the Table 2 in the same manner as in the Test Experiment 1 using Tyromyces palustris as fungus. The results are shown in the Table 2.

TABLE 2

| | Wood Preservative Composition | | |
|---|---|---|---|
| | Wood Preservative and Its Content in the Composition (weight %) | | Content of Phenylxylyl-ethane (weight %) | Average Decrease in Weight (weight %) |
| Example 1 | A-1 | 0.5 | 94.5 | 0.8 |
| Comparative 7 | A-1 | 0.5 | — | 15.3 |
| Example 2 | A-2 | 0.5 | 94.5 | 0.7 |
| Comparative 8 | A-2 | 1.0 | — | 11.4 |
| Example 3 | A-3 | 0.5 | 94.5 | 1.2 |
| Comparative 3 | A-3 | 0.5 | — | 10.7 |
| Example 4 | A-4 | 0.5 | 94.5 | 2.0 |
| Comparative 4 | A-4 | 1.0 | — | 18.7 |
| Example 5 | A-5 | 0.5 | 94.5 | 1.0 |
| Comparative 5 | A-5 | 0.5 | — | 1.7 |
| Example 7 | A-6 | 0.7 | 94.5 | 0.9 |
| Comparative 9 | A-6 | 0.5 | — | 11.7 |
| Contrast | — | — | — | 23.5 |

TEST EXPERIMENT 3

Wood preservative test was carried out with the wood preservative compositions shown in the Table 3 in the same manner as in the Test Experiment 1 using Coriolus versicolor as fungus. The results are shown in the Table 3.

TABLE 3

| Wood Preservative Composition | | | |
|---|---|---|---|
| | Wood Preservative and Its Content in the Composition (weight %) | Content of Phenylxylylethane (weight %) | Average Decrease in Weight (weight %) |
| Example 8 | A-5  0.5 | 99.5 | 0.5 |
| Example 9 | A-5  0.5 | 50.0 | 0.9 |
| Example 10 | A-5  0.5 | 20.0 | 2.6 |
| Comparative 10 | A-5  0.5 | — | 10.7 |
| Contrast | — | — | 35.5 |

What is claimed is:

1. A wood preservative composition which comprises a wood preservative in an amount of 0.05–2% by weight and phenylxylylethane in an amount of not less than 1% by weight and in an amount of 5–500 parts by weight in relation to one part by weight of the wood preservative, said wood preservative being at least one member selected from the group consisting of 3-iodo-2-propynylbutylcarbamate, 3-bromo-2,3-diiodo-2-propenylethylcarbonate, p-chlorophenyl-3-iodopropargylformal, 2-thiocyanomethylthiobenzothiazole, 1-((2-(2',4'-dichlorophenyl)-4-propyl-1,3-dioxolan-2-yl)methyl)-1H-1,2,4-triazole and N,N-dimethyl-N'-phenyl-(N'-fluorodichloromethylthio)sulfamide.

2. The wood preservative composition as claimed in claim 1 which further contains an aliphatic petroleum solvent mainly composed of paraffins and having an aniline point of 69 or an aromatic petroleum solvent mainly composed of alkylbenzenes and having an aniline point of 16 or both.

3. The wood preservative composition as claimed in claim 1 which further contains an alkyl resin having 66% oil length by tall oil.

* * * * *